United States Patent [19]
Strickland et al.

[11] 3,990,118
[45] Nov. 9, 1976

[54] JOINT PROSTHESIS
[75] Inventors: James W. Strickland, Indianapolis; Allan Vegell, Fort Wayne; Terry L. Woodling, Warsaw, all of Ind.
[73] Assignee: Bio-Dynamics, Inc., Indianapolis, Ind.
[22] Filed: Sept. 22, 1975
[21] Appl. No.: 615,599

Related U.S. Application Data
[63] Continuation of Ser. No. 519,518, Oct. 31, 1974, abandoned.

[52] U.S. Cl. ............................ 3/1.91; 128/92 C; 403/157
[51] Int. Cl.² .......................................... A61F 1/24
[58] Field of Search ........................ 3/1.9–1.913, 3/1; 128/92 C, 92 R; 403/157

[56] References Cited
UNITED STATES PATENTS

| | | | |
|---|---|---|---|
| 1,101,682 | 6/1914 | Cook | 403/157 |
| 3,506,982 | 4/1970 | Steffee | 3/1.91 |
| 3,638,243 | 2/1972 | Campbell, Jr. et al. | 3/1.91 |
| 3,760,427 | 9/1973 | Schultz | 3/1.91 |
| 3,765,033 | 10/1973 | Goldberg et al. | 3/1.911 |
| 3,837,008 | 9/1974 | Bahler et al. | 3/1.91 |

OTHER PUBLICATIONS
"Metal Alloplasty of the Knee Joint" by E. J. Moeys, *The Journal of Bone & Joint Surgery*, vol. 36–A, No. 2, Apr. 1954, pp. 363–367.

*Primary Examiner*—Ronald L. Frinks
*Attorney, Agent, or Firm*—Woodard, Weikart, Emhardt & Naughton

[57] ABSTRACT

An implantable prosthetic joint comprising a first member and a second member, both of which include a stem portion implantable in bone. The first member has a neck portion and a protuberant head portion attached to the neck portion. The second member has a head-receiving cavity and a slot in communication with the cavity to provide hinge-like motion of the joint as the neck portion is moved within the slot and the head portion rotated within the cavity. The head-receiving portion of the second member includes a transverse channel communicating with the cavity and a transverse slot communicating with the transverse channel whereby the head and neck portion of the first member may be inserted into the head-receiving portion of the second member in a direction transverse to the plane established by the hinge-like motion of the first member relative to the second member as the neck portion of the first member moves along the channel in the head-receiving portion of the second member.

16 Claims, 11 Drawing Figures

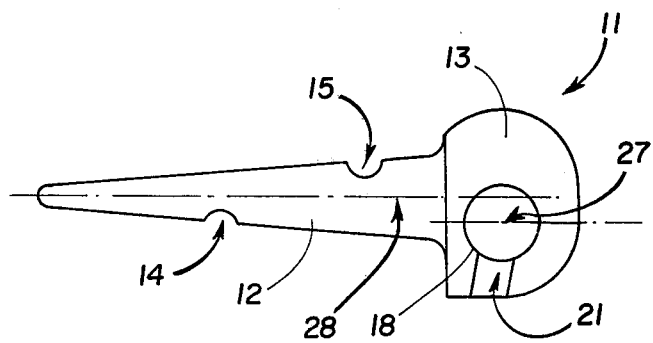
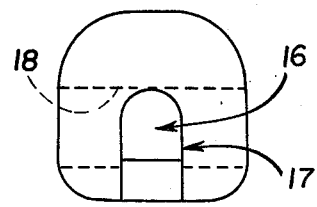
Fig. 1               Fig. 3
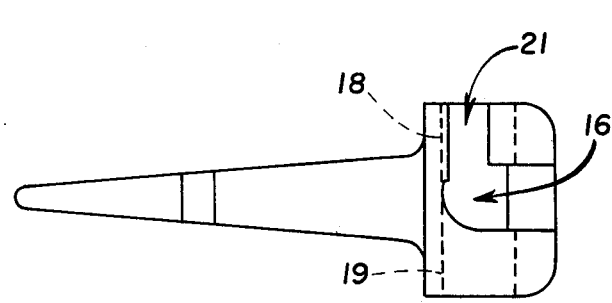
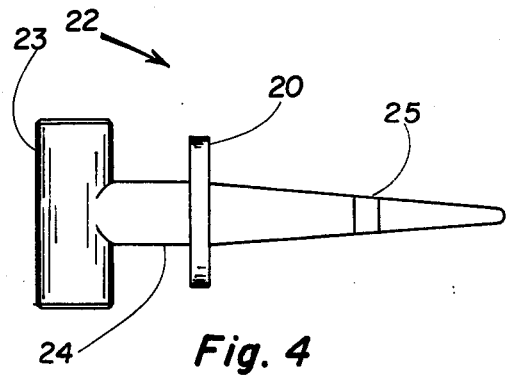
Fig. 2               Fig. 4
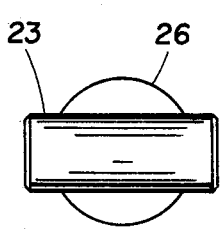
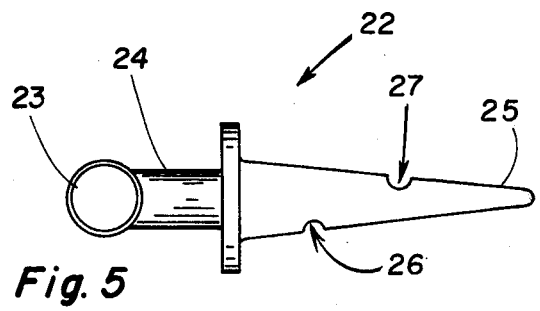
Fig. 6               Fig. 5
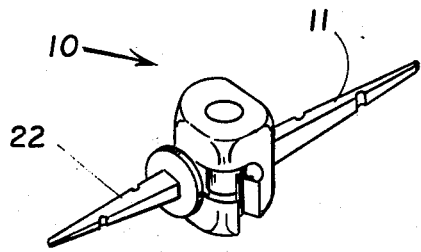
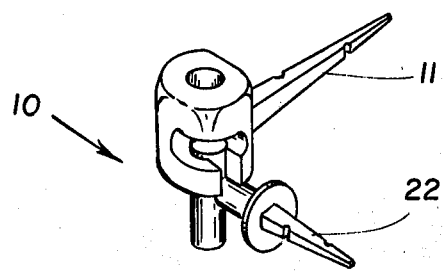
Fig. 7A              Fig. 7B

JOINT PROSTHESIS

This is a continuation of application Ser. No. 519,518, filed Oct. 31, 1974, now abandoned.

BACKGROUND OF THE INVENTION

1. Field of the Invention:

The invention is in the field of bone prostheses.

2. Description of the Prior Art:

In the past, various hinge-like prosthetic joints have been disclosed which comprise a pair of pivoted members fastened together by some type of pin. Examples of these pinned joints include U.S. Pat. Nos. 3,772,709 to Swanson; 3,656,186 to Dee; 3,765,033 to Goldberg et al.; 2,696,817 to Prevo; and 3,466,669 to Flatt.

Ball and socket joints for providing a primarily hinge-type motion are shown in U.S. Pat. Nos. 3,694,821 to Moritz and 3,506,982 to Steffee. The Steffee joint is intended primarily for fingers and the two components of the joint are assembled through a snap-in fit along a line more or less colinear with the direction of orientation of the stems of the joint components when the finger is in its straight or extended position. Another somewhat similar joint is shown in U.S. Pat. No. 3,760,427 to Schultz. In the Schultz joint, the ball of the ball-and-socket arrangement is inserted into the socket member from a direction above the socket in a line which lies within the plane of pivotal motion between the two joint members. Subsequent to this insertion of the ball into the socket, the socket member is inserted further into the receiving bone to cover the opening through which the ball is inserted.

In a joint of the type above described wherein the insertion of the ball into the socket is more or less direct or in a straight line with the extended position of the joint, the joint is subject to forces opposite to those necessary for insertion along this same line. In such a joint there also is a considerable freedom of movement in lateral directions as well as along the main direction of hinge-like motion between the joint components, and this can be a disadvantage especially in the case of an arthritic hand wherein the joints are subject to lateral forces; the joint would be more advantageous if resistant to these lateral forces. The insertion of the ball member into the socket of the socket member, such as described in the Schultz patent, provides an additional implantation step due to the necessity of a second stage of insertion of the socket member further into the bone after assembly.

SUMMARY OF THE INVENTION

One embodiment of the present invention is an implantable prosthetic joint comprising a first member including a stem portion for affixing the first member to bone, a neck portion on one end of the stem portion, and a protuberant head portion on the neck portion, and a second member comprising, a stem portion for affixing the second member to bone, and a head-receiving portion on one end of the stem portion of the socketed member having a headed portion receiving cavity removably retaining the headed portion of the first member, an elongated slot intersecting the cavity slidably receiving the neck portion of the first member permitting hinged motion of the first member relative to the second member in a first plane through movement of the neck portion along slot, and insertion means for inserting the head portion of the first member into the cavity in a direction transverse to said plane.

It is an object of the present invention to provide a hinge-like joint having a headed member and a head-receiving member wherein the head of the headed member is inserted into the head-receiving member in a direction transverse to the plane of hinge-like motion of the one member relative to the other member.

It is a further object of the present invention to provide a hinge-like joint wherein lateral movement of one joint member relative to the other joint member is substantially reduced.

Further objects and advantages of the present invention shall be apparent from the following detailed description and accompanying figures.

BRIEF DESCRIPTION OF THE DRAWINGS

FIG. 1 is a side view of the proximal component of a prosthetic joint according to the present invention.

FIG. 2 is a bottom view of the proximal component of FIG. 1.

FIG. 3 is an end view of the component of FIG. 1.

FIG. 4 is a top view of the distal component associated with the proximal component of FIGS. 1 through 3.

FIG. 5 is a side view of the component of FIG. 4.

FIG. 6 is an end view of the component of FIGS. 4 and 5.

FIG. 7A is a perspective view of the assembled joint utilizing the components of FIGS. 1 through 6, in an assembled condition with the joint in its open or extended position.

FIG. 7B is a perspective view of the joint of FIG. 7A in a partially disassembled condition with the joint in its bent position at about 90°.

DESCRIPTION OF THE PREFERRED EMBODIMENT

Figure 8:
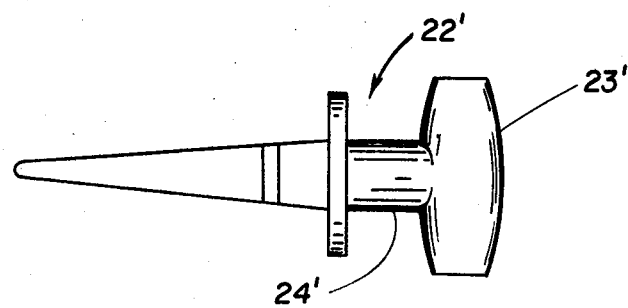
FIG. 8 is a top view of a modified form of the distal component of FIGS. 4 through 6.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring in particular to FIG. 7A, there is shown an interphalangeal prosthetic joint 10 for the human hand. Joint 10 comprises a proximal component 11 which is shown in greater detail in FIGS. 1 through 3, and a distal component 22. As shown in FIG. 1, the proximal component 11 has a stem portion 12 and a head-receiving portion 13. Proximal component 11 is an ultra high molecular weight polyethylene material, and stem portion 12 is tapered for insertion into the bone in the first row of phalanges, that row nearest the hand. Stem portion 12 includes slots 14 and 15 to enhance the anchoring of stem 12 within the bone. As shown in FIGS. 2 and 3, head-receiving portion 11 has a head-receiving cavity 16 communicating with a slot 17 in the distal face of portion 13. A transverse channel 18 extends from one face of head-receiving portion 13 to cavity 16 and has an extending channel portion 19 continuing to the opposite face of head-receiving portion 13. A transverse slot 21 communicating with tranverse channel 18 extends from the first face of head-receiving portion 13 to cavity 16 intersecting with slot 17, as best shown in FIG. 2.

Referring now to FIGS. 4 through 6, there is shown distal component 22 of interphalangeal joint 10 (FIG. 7). Distal component 22 includes a cylindrical head portion 23, cylindrical neck portion 24 and stem portion 25 for anchoring distal component 22 in the bone of the second row of phalanges. Stem portion 25 includes transverse slots 26 and 27 to assist in affixing the stem portion within the phalangeal bone. Distal component 22 is preferably a cast Cobalt-Chromium-Molybdenum alloy for surgical implants or other approved metal for surgical implants. Distal component 22 further includes a disc-shaped guard portion 20 separating the neck 24 from stem 25, which guard portion is adjacent the end face of the proximal component after assembly of the joint.

As best shown in FIG. 7B, and after stems 12 and 25 have been implanted in the appropriate bones, interphalangeal joint 10 is assembled by orienting stems 12 and 25 at approximately a 90° angle and inserting head 23 into transverse slot 18 and cavity 16 such that the leading end of head 23 passes through portion 19 of transverse slot 18. Head 23 is fully inserted into transverse channel 18 such that the leading end of head 23 is essentially flush with the second face of head-receiving portion 13. Obviously, as head 23 is inserted through transverse channel 18, neck 24 passes along slot 21 which is provided for that purpose. The width of slot 21 is slightly less than the diameter of neck 24 so that neck 24 must be forced along slot 21, and when neck 24 reaches the intersecting area between slot 17 and slot 21, it snaps into place. The width of slot 17, however, is slightly wider than neck 24 so that neck 24 may freely move in slot 17 to provide the hinge-like motion of the joint.

This hinge-like motion is produced by the rotation of cylindrical head 23 within cavity 16 and transverse channel 18 while neck 24 moves along slot 17. The extent of motion of distal component 22 relative to proximal component 11 is about 90°, extending from the perpendicular orientation at assembly, as shown in FIG. 7B, to a more or less "in-line" orientation in which the finger is fully extended and the stems of the two components of joint 10 are more or less in parallel orientation, as shown in FIG. 7A.

The axis of rotation of cylindrical head 23 within transverse channel 18 is indicated generally at point 27 in FIG. 1. It can be seen that this center of rotation is located below the center line 28 of stem 12 in order to provide freer movement of the joint within the hand. Additionally, with the sizing of slot 17 only slightly greater than the diameter of neck 24, and the extension of one end of cylindrical head 23 into transverse slot portion 19, joint 10 is essentially restricted to one direction of motion, the hinge-like motion of proximal component 11 relative to distal component 22. Lateral motion of distal component 22 relative to proximal component 11 is effectively prevented, thereby greatly resisting ulnar deviation often encountered in an arthritic hand wherein such prosthetic joints are implanted.

Figure 9:
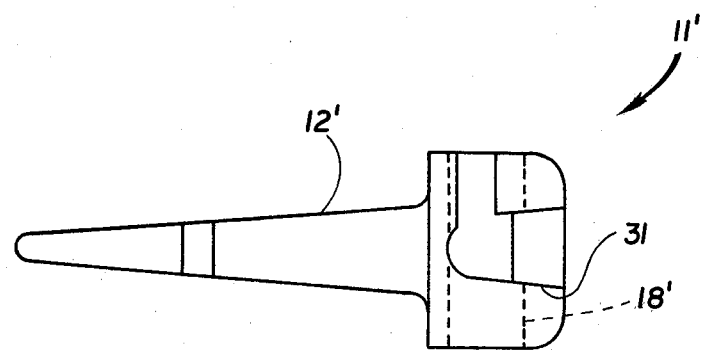
FIG. 9 is a bottom view of a proximal component associated with the distal component of FIG. 8 and which is a modification of that shown in FIGS. 1 through 3.
Figure 10:
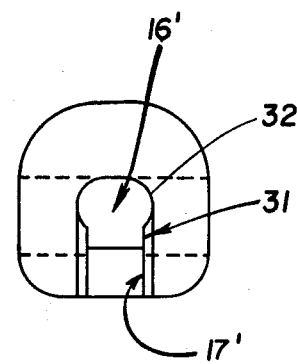
FIG. 10 is an end view of the proximal component of FIG. 9.

Referring now to FIGS. 8 through 10, there are shown the components of a prosthetic joint slightly modified from the joint 10 of FIGS. 1 through 7. The joint of FIGS. 8 through 10 is metacarpal-phalangeal, or knuckle, joint of the hand. The joint whose components are shown in FIGS. 8 through 10 provides for a small amount of lateral movement at the joint by modifying the head of the distal component and the principal slot of the proximal component. In the implantation of the joint shown in FIGS. 8 through 10, the stem portion of the proximal component is affixed within a metacarpal bone and the stem of the distal component is affixed in the associated phalangeal bone.

As shown in FIG. 8, the distal component 22' is the same as distal component 22 except that head 23' is barrel-shaped rather than cylindrical. As shown in FIGS. 9 and 10, proximal component 11' is the same as proximal component 11 except for modifications to slot 17. The walls 31 of slot 17' each taper, at an angle of about 5° from the direction of the center line of stem 12', from the end face of proximal component 11' to cavity 16'. This taper enables lateral motion of neck 24' within slot 17'. Head 23' of the distal component is barrel-shaped with the largest diameter portion lying within cavity 16' and tapered ends of head 23' lying in transverse channel 18'. The tapered ends of head 23' are of lesser diameter than the diameter of transverse channel 18', permitting a certain degree of "rocking" motion of the distal component relative to the proximal component. Slot 17' is further modified in that its uppermost portion 32 is elongated into an elliptical shape having its principal axis in a lateral direction, as best shown in FIG. 10. This configuration of the uppermost portion 32 of slot 17 permits a greater degree of freedom of neck portion 24' of the distal component when distal component 22' and proximal component 11' are oriented in the unbent, or extended, position similar to the position of joint 10 in FIG. 7A wherein the stems of each of the components are oriented essentially parallel.

The prosthetic joint illustrated in FIGS. 1 through 7 is an interphalangeal joint adapatable for use in place of any of the interphalangeal joints of the human hand. The joint whose components are illustrated in FIGS. 8 through 10 is intended for use as a metacarpal-phalangeal joint and may be sized as appropriate for the size of joint being replaced. For example, a smaller and larger size for the joint of FIGS. 8 through 10 is preferred, the smaller joint being used for small hands or the small knuckle joint of an average size hand, and the larger size being used for the larger metacarpal-phalangeal joints of the hand. Other hinge-type joints embodying the present invention may, of course, be used to replace other hinge-type joints in humans or animals.

While there have been described above the principles of this invention in connection with specific apparatus, it is to be clearly understood that this description is made only by way of example and not as a limitation in the scope of the invention.

What is claimed is:
1. An implantable prosthetic joint comprising:
   a. a first component including,
      1. a stem portion including stem means for affixing the first component to bone,

2. a neck portion on one end of the stem portion, and
3. a protuberant head portion on the neck portion; and
b. a second component including,
1. a stem portion including stem means for affixing the second component to bone, and
2. a head-receiving portion on one end of the stem portion having a head-receiving cavity removably retaining the headed portion of the first member, an elongated principal slot defined by a first side wall and a second side wall intersecting said cavity and slidably receiving the neck portion of the first member, permitting hinged motion of the first member relative to the second member in a first plane through movement of the neck portion along the principal slot in its longest direction between said first and second side walls, and having insertion means for inserting the head portion of the first member into said cavity in a direction transverse to said first plane, the insertion means comprising head-receiving channel extending from a lateral first face of the head-receiving portion of the second component in a direction transverse to said first plane of motion and communicating with said cavity and having an elongated transverse slot intersecting said transverse channel and sized to allow passage of the neck portion of the first component therethrough, the transverse slot intersecting the principal slot.

2. The joint of claim 1 in which the transverse slot of the head-receiving portion of the second member is, at least in the vicinity of the principal slot, defined by a flexible material making the transverse slot slightly narrower than the thickness of the neck portion of the first member, thereby providing a snap-in fit as the neck portion is inserted past the transverse slot into the principal slot.

3. The joint of claim 1 in which the head portion of the first component is elongated having a principal dimension transverse to the neck portion of the first member.

4. The joint of claim 3 in which the transverse channel extends beyond the cavity to an opening in a second face of the head-receiving portion of the second component, said second face being opposite the first face of the head-receiving portion of the second component.

5. The joint of claim 4 in which the ends of the elongated head portion are received in portions of the transverse channel outside the cavity in the head-receiving portion of the second component.

6. The joint of claim 5 in which one end of the elongated head portion of the first component is adjacent the opening in the second face of the head-receiving portion of the second component within a portion of the transverse channel.

7. The joint of claim 6 in which the head-receiving portion of the second member is, along the transverse slot, a flexible plastic material with the transverse slot being slightly narrower than the thickness of the neck portion of the first member until the transverse slot is in communication with the principal slot of the head-receiving portion of the second component, thereby providing a snap-in fit as the neck portion is inserted past the transverse slot into the principal slot.

8. The joint of claim 7 in which the principal slot at its point furthest from the transverse slot terminates in an opening wider than the slot.

9. The joint of claim 1 in which the axis of rotation of the head portion of the first component in the second component does not intersect the centerline of the stem portion of the second component.

10. The joint of claim 1 which further comprises a thin shield portion, between the stem portion and neck portion of the first component, extending outwardly of the neck portion and said stem portion.

11. The joint of claim 1 in which the stem portion of each joint component has a principal dimension, the directions of the principal dimensions being essentially aligned when the joint is in its extended position and being essentially perpendicular when the joint is in its bent position.

12. The joint of claim 11 in which the elongated transverse slot is located such that the joint is in its bent position when the neck portion of the first component passes through said elongated transverse slot and the neck portion is misaligned with said elongated transverse slot to prevent passage therethrough in positions other than said bent position.

13. The joint of claim 3 in which the principal slot at its point furthest from the transverse slot terminates in an opening wider than the principal slot, and in which the head portion of the first component is tapered from a generally centrally located thickest portion in the vicinity of the neck portion to narrower portions in each direction along the principal dimension of the head portion, thereby permitting a limited rocking motion of the first component relative to the second component when the neck of the first component is in said wider opening of the principal slot.

14. The joint of claim 13 in which the elongated principal slot flares outwardly from a smallest width at its intersection with the cavity.

15. The joint of claim 1 in which the transverse slot in the second component is located such that the neck of the first component is rotated more than 90° from a fully extended position of the joint when the neck portion passes through the transverse slot for assembly of the joint.

16. The joint of claim 1 in which the transverse slot in the second component is located such that the neck of the first component is rotated essentially 90° from a fully extended position of the joint when the neck portion passes through the transverse slot for assembly of the joint.

* * * * *